(12) United States Patent
Hermansson

(10) Patent No.: US 8,298,206 B2
(45) Date of Patent: Oct. 30, 2012

(54) BELTED ABSORBENT ARTICLE

(75) Inventor: Kent Hermansson, Västra Frölunda (SE)

(73) Assignee: SCA Hygiene Products AB, Göteborg (SE)

( * ) Notice: Subject to any disclaimer, the term of this patent is extended or adjusted under 35 U.S.C. 154(b) by 130 days.

(21) Appl. No.: 12/682,127

(22) PCT Filed: Oct. 10, 2007

(86) PCT No.: PCT/SE2007/050731
§ 371 (c)(1),
(2), (4) Date: Apr. 8, 2010

(87) PCT Pub. No.: WO2009/048361
PCT Pub. Date: Apr. 16, 2009

(65) Prior Publication Data
US 2010/0211039 A1    Aug. 19, 2010

(51) Int. Cl.
*A61F 13/15*    (2006.01)

(52) U.S. Cl. ........ 604/389; 604/391; 604/392; 604/387; 604/390; 604/394; 604/396

(58) Field of Classification Search ................. 604/391, 604/392, 387, 390, 394, 396, 389
See application file for complete search history.

(56) References Cited

U.S. PATENT DOCUMENTS

| | | | |
|---|---|---|---|
| 4,946,527 A | 8/1990 | Battrell | |
| 5,374,262 A | 12/1994 | Keuhn, Jr. et al. | |
| 5,386,595 A | 2/1995 | Kuen et al. | |
| 5,476,702 A | 12/1995 | Datta et al. | |
| 5,722,968 A | 3/1998 | Datta et al. | |
| 6,689,116 B1 * | 2/2004 | Ekdahl et al. | 604/391 |
| 2001/0023341 A1 | 9/2001 | Karami | |
| 2002/0052584 A1 | 5/2002 | Forgar | |
| 2002/0062118 A1 * | 5/2002 | Almberg et al. | 604/392 |
| 2002/0193776 A1 | 12/2002 | Fernfors | |
| 2005/0022291 A1 | 2/2005 | Coates et al. | |

FOREIGN PATENT DOCUMENTS

| | | |
|---|---|---|
| DE | 198 13 334 | 9/1999 |
| DE | 10 2005 044 687 A1 | 3/2007 |
| EP | 0 605 012 A1 | 7/1994 |
| EP | 0 605 013 A1 | 7/1994 |
| EP | 1 035 818 | 6/1999 |
| FR | 2 586 558 | 3/1987 |
| GB | 2 080 093 A | 3/1982 |
| JP | H10-505517 A | 6/1998 |
| JP | 2005-296557 A | 10/2005 |

(Continued)

OTHER PUBLICATIONS

Office Action dated Jul. 13, 2011, issued in the corresponding Russian Patent Application No. 2010118470, and an English Translation thereof.
International Search Report for PCT/SE2007/050731 completed Jun. 26, 2008.
Written Opinion for PCT/SE2007/050731 completed Jun. 26, 2008.
Extended European Search Report dated Apr. 5, 2012 issued in corresponding European Application No. 07835316.6.

(Continued)

*Primary Examiner* — Jacqueline F. Stephens
(74) *Attorney, Agent, or Firm* — Buchanan Ingersoll & Rooney PC

(57) ABSTRACT

An absorbent article includes a belt and an absorbent structure. The absorbent structure is fastened to the belt via an article fastening means having a form such that the article fastening means does not fold or bend upwards under the forces present when the diaper is assembled.

12 Claims, 3 Drawing Sheets

FOREIGN PATENT DOCUMENTS

| | | |
|---|---|---|
| WO | 96/03101 A1 | 2/1996 |
| WO | WO 02/05739 A1 | 1/2002 |
| WO | WO 03/007865 A1 | 1/2003 |
| WO | WO 03/017903 | 3/2003 |
| WO | WO 03/017904 | 3/2003 |
| WO | WO 2006/065177 A1 | 6/2006 |

OTHER PUBLICATIONS

English translation of Notification of Reasons for Refusal issued May 29, 2012 by the Japanese Patent Office in corresponding Japanese Application No. 2010-528828.

* cited by examiner

BELTED ABSORBENT ARTICLE

TECHNICAL FIELD

The present invention provides an absorbent article comprising a belt and an absorbent structure. The absorbent structure is fastened to the belt via an article fastening means having a form and orientation such that the article fastening means does not fold or turn up under the forces present when the diaper is being worn.

BACKGROUND OF THE INVENTION

Absorbent articles such as diapers and incontinence guards are worn by incontinent persons to manage body waste such as urine or faeces. They generally comprise two important features: an absorbent structure which absorbs and manages the body waste, and components which keep the absorbent structure in place on the body of the wearer under a range of activities (e.g. walking, sitting or lying down).

Diapers and incontinence guards can be classified according to their structure. Pant diapers resemble normal underwear, and are applied to a wearer by being pulled up the wearer's legs, in the same way as regular underwear. Traditional diapers have front and rear portions which are fastened to one another around the waist of the wearer.

Belted absorbent articles, such as belt diapers, have a belt which is first fastened around the waist of a wearer. Belted absorbent articles are popular with incontinent adults as they can be changed by the wearer themselves while standing up. After fastening the belt, the absorbent structure is then brought between the legs of the wearer and fastened by article fastening means to the belt. In such articles, at least a portion of the waistband of the article only comprises the belt (i.e. the front and rear portions of the absorbent structure are not directly fastened to one another around the waist of the wearer). The present invention concerns belted absorbent articles.

Examples of belted articles are provided in WO 02/05739, WO 06/065177, WO 03/017904 and WO 03/017903.

GB 2 080 093 discloses a traditional diaper (i.e. not a belt diaper) which has strips of tape aligned in the direction of the leg elastics.

Typically, little attention has been paid to the form and/or placement of the article fastening means used to fasten the absorbent structure of a belted absorbent article to the belt. In the interests of simplicity and manufacturing efficiency, article fastening means to date have usually comprised a square or rectangle of material which is applied to the absorbent structure such that one edge is parallel to the front (longitudinal) edge or the transverse edge in the front region of the absorbent structure.

However, the primary forces in the waist and hip region of such belted absorbent articles when being worn are directed from the hip region of the belt inwards and downwards towards the crotch of the wearer (see arrow X in FIG. 2). The article fastening means of the prior art are by no means ideal in such situations, and—under such forces—tend to fold upwards or be uncovered at their lower edges. This can lead to problems with poor fastening ability, as the entire article fastening means is not in full contact with the corresponding reception surface. Poor fastening in turn leads to poor fit and the risk of leakage. Furthermore, article fastening means which is exposed can fasten undesirably to the wearer's clothes or bedclothes.

There thus remains a need for a belted absorbent article in which the above problems are addressed in a simple and effective manner.

SUMMARY OF THE INVENTION

The present invention is based on the realisation that the form and alignment of the article fastening means are important for obtaining a belted absorbent article which poor fit, risk of leakage and undesirable fastening to other articles are reduced.

The invention thus provides an absorbent article, such as a diaper or an incontinence guard, said article comprising a belt and an absorbent structure. The belt comprises an article reception surface. The absorbent structure extends in the longitudinal (L) and transverse (T) directions and has a longitudinal centre line (L1) and opposing first and second longitudinal end regions. Each of said longitudinal end regions has a perimeter constituted by a transversely extending end edge and a pair of opposed longitudinal edges. The first longitudinal end region of said absorbent structure is attached to the belt.

The absorbent structure comprises at least one article fastening means at the second longitudinal end region thereof, said article fastening means adapted to fasten to the article reception surface on the belt such that the absorbent article adopts a pant-like shape in use. The article fastening means has a substantially circular shape in the L-T plane.

Suitably, the first longitudinal end of said absorbent structure is attached to the belt via at least one article fastening means located at the first longitudinal end of the absorbent structure, said article fastening means having a circular shape. Alternatively, the first longitudinal end of said absorbent structure is permanently attached to the belt.

Preferably, the maximum extension of the article fastening means in a direction perpendicular to a force line (X) which passes through the centre of the circular article fastening means and which makes an angle with the longitudinal centre line (L1) of the absorbent structure of between 5° and 85°, preferably between 10° and 80°, more preferably between 15° and 45° is less than 3 cm, preferably less than 2 cm, more preferably less than 1 cm.

Suitably, the belt consists of article reception surface on the garment-facing side thereof.

Definitions

The term "absorbent article" refers to products that are placed against the skin of the wearer to absorb and contain body exudates, like urine, faeces and menstrual fluid. The invention mainly concerns disposable absorbent articles, which means articles that are not intended to be laundered or otherwise restored or reused as an absorbent article after the first use.

The "absorbent structure" of the absorbent article is that component of the absorbent article which receives and stores exuded bodily fluids. As such, it comprises at least an absorbent core. The absorbent structure may be permanently attached to the belt of a belted absorbent article, or may be removably attached. Typically, the absorbent structure is manufactured before being joined to the belt of a belted absorbent article. It therefore comprises a separate component of the absorbent article to the belt.

BRIEF DESCRIPTION OF THE DRAWINGS

The invention may be more readily understood by reference to the attached drawings which, by way of example only, schematically illustrate various embodiments of the invention.

DETAILED DESCRIPTION OF PREFERRED EMBODIMENTS

Figure 1:
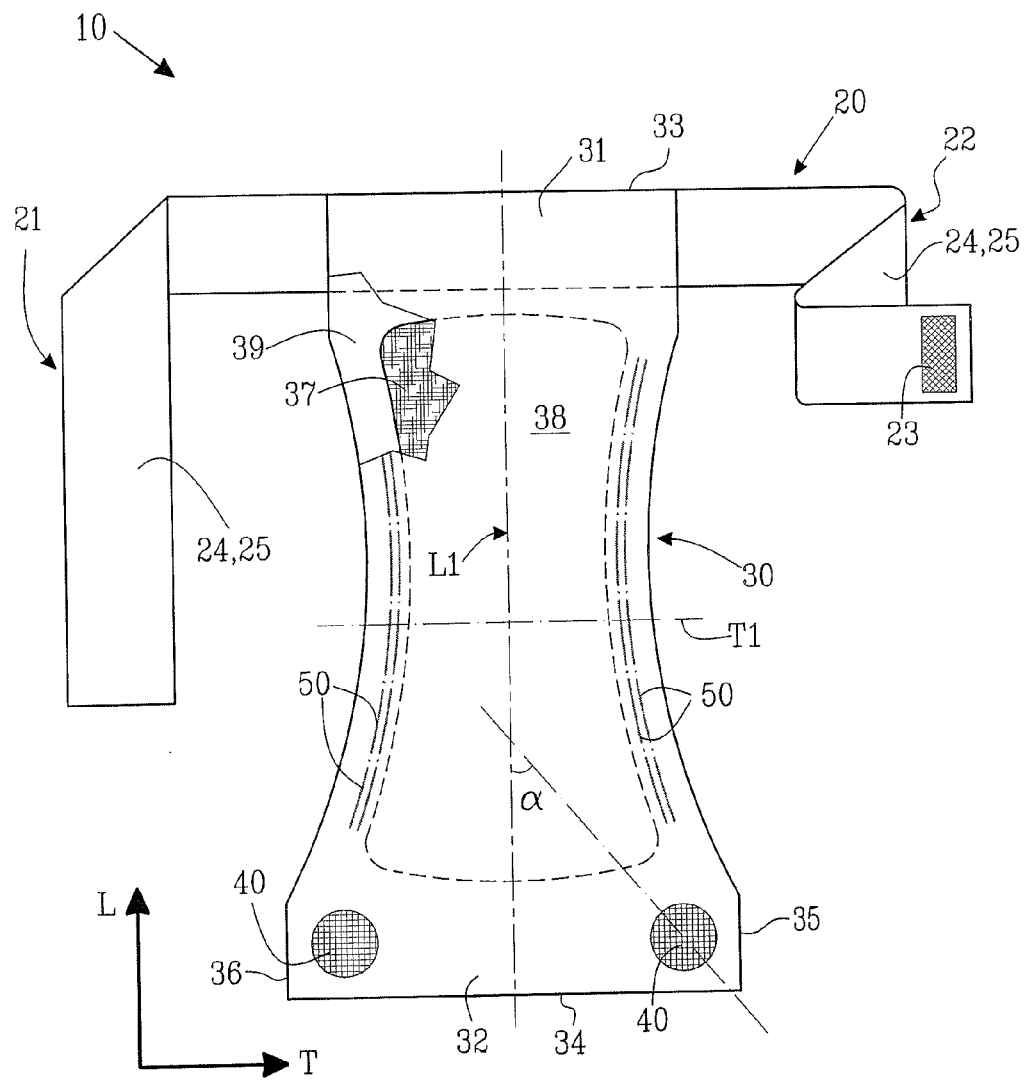
FIG. 1 shows an open belt-diaper according to the invention, seen from the wearer-facing side and with all elastic components of the absorbent structure fully extended.

FIG. 1 shows an absorbent article 10 according to the invention, seen from the wearer—facing side (inside) and with all elastic components of the absorbent structure 30 fully extended. The article comprises a belt 20 and an absorbent structure 30. In FIG. 1, the belt 20 is open.

In use, the belt 20 is fastened about the wearer's waist, where it acts to hold the absorbent structure 30 in place. The belt 20 of FIG. 1 comprises two belt halves, 21, 22, although it is conceivable that a single belt is present, which wraps completely around the waist of the wearer. The belt 20 of FIG. 1 also comprises belt attachment means 23 which fastens to belt reception surface 25, so that the belt can be fastened around the waist of the wearer. If the belt attachment means 23 comprises hook material of a hook-and-loop (e.g. Velcro®) fastener, belt reception surface 25 suitably comprises loop material. Likewise, if the belt attachment means 23 comprises adhesive material, the belt reception surface 25 suitably comprises a plastic film material to which the adhesive material can fasten, preferably in a releasable manner. The belt 20 may comprise a single length of belt material, to which the absorbent structure 30 is attached, or may comprise two separate lengths of belt material, each of which is attached to the absorbent structure 30.

The width of the belt 20 should be between circa 50 mm and 250 mm. The belt 20 may comprise nonwoven material or plastic film, or laminates thereof. In a preferred embodiment, the belt 20 comprises a laminate of at least one nonwoven material and at least one plastic film. The belt 20 may have elastic properties in at least one region thereof, and in at least one direction, preferably in the length direction of the belt. Elastic properties may be provided by the use of one or more elastic components, such as e.g. elastic threads, elastic nonwoven materials or elastic films. Belts 20 with elastic properties are particularly useful. The belt 20 is desirably breathable, and the material constituting the belt 20 may be perforated or porous or the belt 20 may be spaced from the skin of the wearer by spacer fabric or spacer elements.

The belt 20 comprises an article reception surface 24, which is preferably the same material as belt reception surface 25. Indeed, a single reception surface (e.g. of nonwoven material) may constitute both the article reception surface 24 and the belt reception surface 25. The article reception surface 24 is located on the outside (garment-facing) surface of the belt 20 when worn. Article reception surface 24 and belt reception surface 25 may each comprise separate pieces of material which are joined to the belt 20 during manufacture, or the wearer-facing surface of the belt 20 may itself consist of one or both of these reception surfaces 24, 25 (as shown in FIG. 1).

The absorbent structure 30 is the component of the absorbent article 10 which receives and stores exuded bodily fluids. It extends in the longitudinal (L) and transverse (T) directions as shown in FIG. 1, and may have any suitable shape, e.g. rectangular, hourglass or T-shaped. In use, the absorbent structure 30 is located between the legs of the wearer so as to cover the wearer's genitals and anal region, and is held in place on the wearer by the belt 20. The absorbent structure 30 has a longitudinal centre line (L1) about which it is symmetrical, and opposing first 31 and second 32 longitudinal end regions. Each of said longitudinal end regions 31, 32 has a perimeter constituted by a transversely extending end edge 33, 34 and a pair of opposed longitudinal edges 35, 36.

Traditionally, belt diapers are applied to a wearer by fastening the belt 20 around the wearer's waist, with the absorbent structure 30 hanging downwards at the wearer's rear. The absorbent structure 30 is then brought between the wearer's legs and fastened to the belt 20 at the wearer's front. In this case, the first longitudinal end region 31 of the absorbent structure 30 will comprise the rear portion of the absorbent article 10, while the second longitudinal end region 32 of the absorbent structure 30 will comprise the front portion of the absorbent article 10. However, the reverse situation is also possible.

In cross-section, the absorbent structure 30 usually comprises a liquid-permeable topsheet 38, a liquid-impermeable backsheet 39 and an absorbent core 37 located between said topsheet 38 and said backsheet 39. However, in certain absorbent structures 30, it may be sufficient to include only an absorbent core 37 and a liquid-impermeable backsheet 39.

The topsheet 38 of the absorbent structure 30 is the layer which lies in contact with the wearer's body when the absorbent article is in use. As such, it should be soft, non-irritating and comfortable against the skin, and bodily fluid should be able to pass through it without hindrance. The topsheet 38 can consist of a nonwoven material, e.g. spunbond, meltblown, carded, hydroentangled, wetlaid etc. Suitable nonwoven materials can be composed of natural fibers, such as woodpulp or cotton fibres, manmade fibres, such as polyester, polyethylene, polypropylene, viscose etc. or from a mixture of natural and manmade fibres. The topsheet may further be composed of tow fibres, which may be bonded to each other in a bonding pattern, as e.g. disclosed in EP-A-1 035 818. Further examples of materials suitable for topsheets are porous foams, apertured plastic films etc. The topsheet 38 may be different in different parts of the absorbent structure 30.

The backsheet 39 of the absorbent structure 30 is the layer which lies furthest from the wearer's body when the article is in use. To protect the wearer's garments from soiling, it should be liquid-impermeable, but is desirably gas-permeable to allow air and vapour to pass in and out of the article so that the warm, damp conditions which can arise in a diaper are reduced. Typically, the backsheet 39 is of a liquid impervious material, such as a thin plastic film, e.g. a polyethylene or polypropylene film, a nonwoven material coated with a liquid impervious material, a hydrophobic nonwoven material, which resists liquid penetration or a laminate comprising plastic films and nonwoven materials. Examples of breathable backsheet materials are porous polymeric films, nonwoven laminates of spunbond and meltblown layers and laminates of porous polymeric films and nonwoven materials. The backsheet 39 may be different in different parts of the absorbent structure 30.

The absorbent core 37 of the absorbent structure 30 acts to receive and contain liquid and other bodily exudates and can be of any conventional kind. As such, it typically comprises absorbent material. Examples of commonly-occurring absorbent materials are cellulosic fluff pulp, tissue layers, highly-absorbent polymers (so called superabsorbents), absorbent foam materials, absorbent nonwoven materials or the like. It is common to combine cellulosic fluff pulp with superabsorbents in an absorbent body. It is also common to have absorbent cores comprising layers of different material with different properties with respect to liquid receiving capacity, liquid distribution capacity and storage capacity. The thin absorbent cores, which are common in for example baby diapers and incontinence guards, often comprise a compressed mixed or layered structure of cellulosic fluff pulp and superabsorbent material. The size and absorbent capacity of the absorbent core 16 may be varied to be suited for different uses such as for infants or for incontinent adults.

The absorbent core 37 may comprise one or more layers which are designed to improve the handling of bodily waste. Such layers are designed to receive a large amount of liquid in a short space of time and distribute it evenly across the absorbent structure 30. They may include so-called transfer, distribution, surge or acquisition layers, and are usually located between the topsheet 38 and the absorbent core 37.

The topsheet 38 and backsheet 39 generally have a similar extension in the plane of the article, while the absorbent core 37 has an extension which is somewhat smaller. The topsheet 38 and backsheet 39 are joined to one another around the periphery of the absorbent core 37, so that the core 37 is enclosed within the envelope formed by the topsheet 38 and the backsheet 39. The absorbent core 37 is at least located in the crotch portion of the absorbent article 10, and may also extend somewhat into the front and rear portions. The topsheet 38, backsheet 39 and other components of the absorbent article 10 may be joined to one another by any means common in the art, e.g. ultrasonic welding, thermal welding or gluing.

In addition, the absorbent structure 30 may comprise one or more elastic elements 50. These help the article 10 fit tightly against the body of the wearer, and are usually present as leg or waist elastic elements (shown as leg elastic elements 50 in FIG. 1).

The first longitudinal end region 31 of said absorbent structure 30 is attached to the belt 20. Attachment of the absorbent structure 30 to the belt 20 may occur substantially in the middle of the belt, as shown in FIG. 1, or towards one end of the belt 20. The attachment may be permanent—i.e. it is not possible to separate the first longitudinal end region 31 of the belt 20 without tearing or otherwise damaging the article 10. Alternatively, the first longitudinal end region 31 of the absorbent structure 30 may be removably attached to the belt 20 via at least one article fastening means 40' located at the first longitudinal end region 31 of the absorbent structure 30, said article fastening means 40' having the shape and alignment of the article fastening means 40 as described herein.

Figure 2:
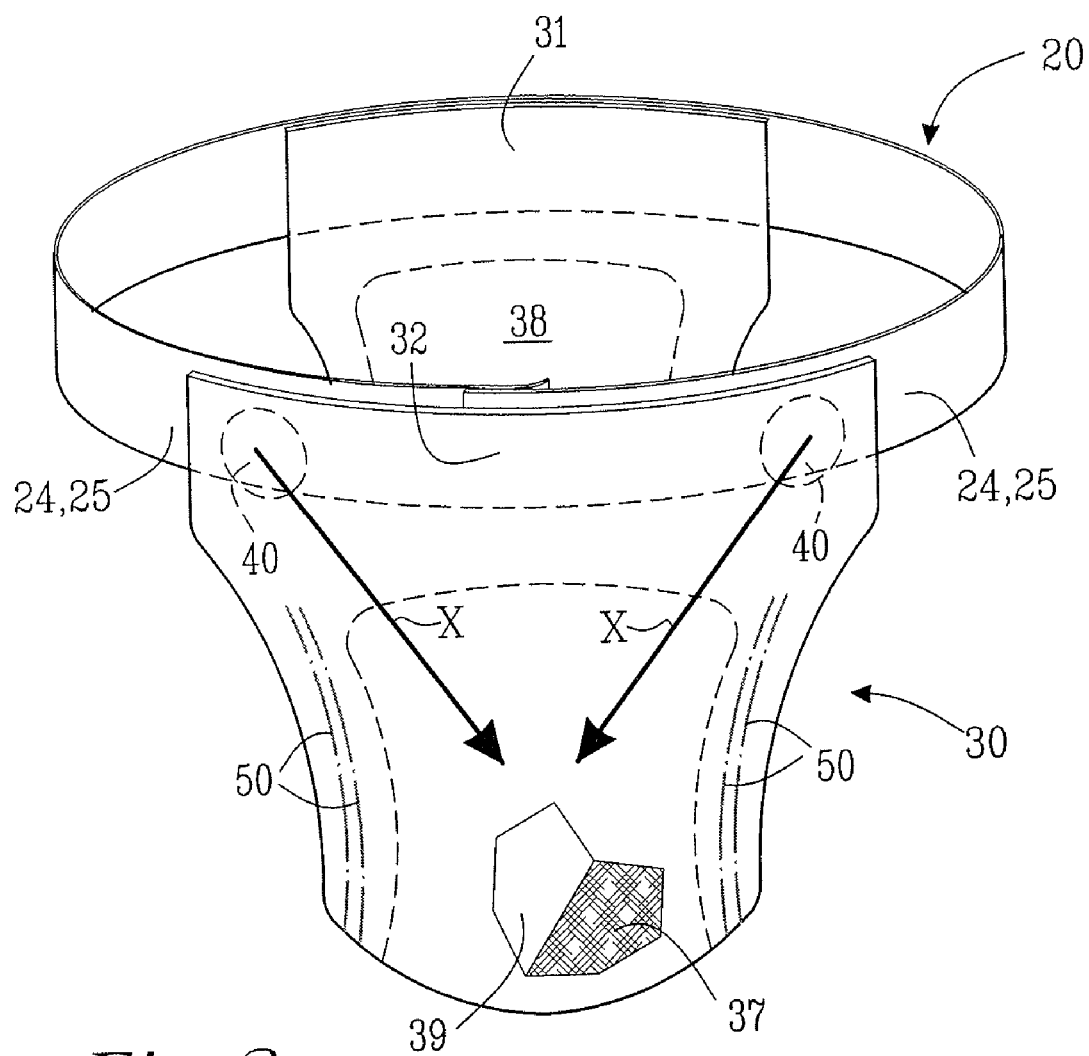
FIG. 2 shows the belt-diaper of FIG. 1 in assembled form.

The absorbent structure 30 comprises at least one (e.g. two) article fastening means 40 at the second longitudinal end region 32 thereof. Preferably, the absorbent structure comprises two article fastening means 40 at the second longitudinal end region 32, each of which is located towards the transverse edge thereof. The article fastening means 40 is adapted to fasten to the article reception surface 24 on the belt 20 such that the absorbent article 10 adopts a pant-like shape in use (FIG. 2). As such, it may comprise a hook portion of a hook-and-loop type fastener (e.g. Velcro®), or an adhesive tab.

The present invention is based on the discovery that the form and alignment of the article fastening means 40 are significant for obtaining a secure fit and for minimizing the risk of the fastening means being undesirably uncovered or turned up. As mentioned above, the primary forces in the waist and hip region of belted absorbent articles when being worn are directed from the hip region of the belt inwards and downwards towards the crotch of the wearer (see arrow X in FIG. 2). The angle α made between the longitudinal centre line of the article and the force arrow X typically lies between 5° and 85°, preferably between 10° and 80°, more preferably between 15° and 45°.

Figure 3:
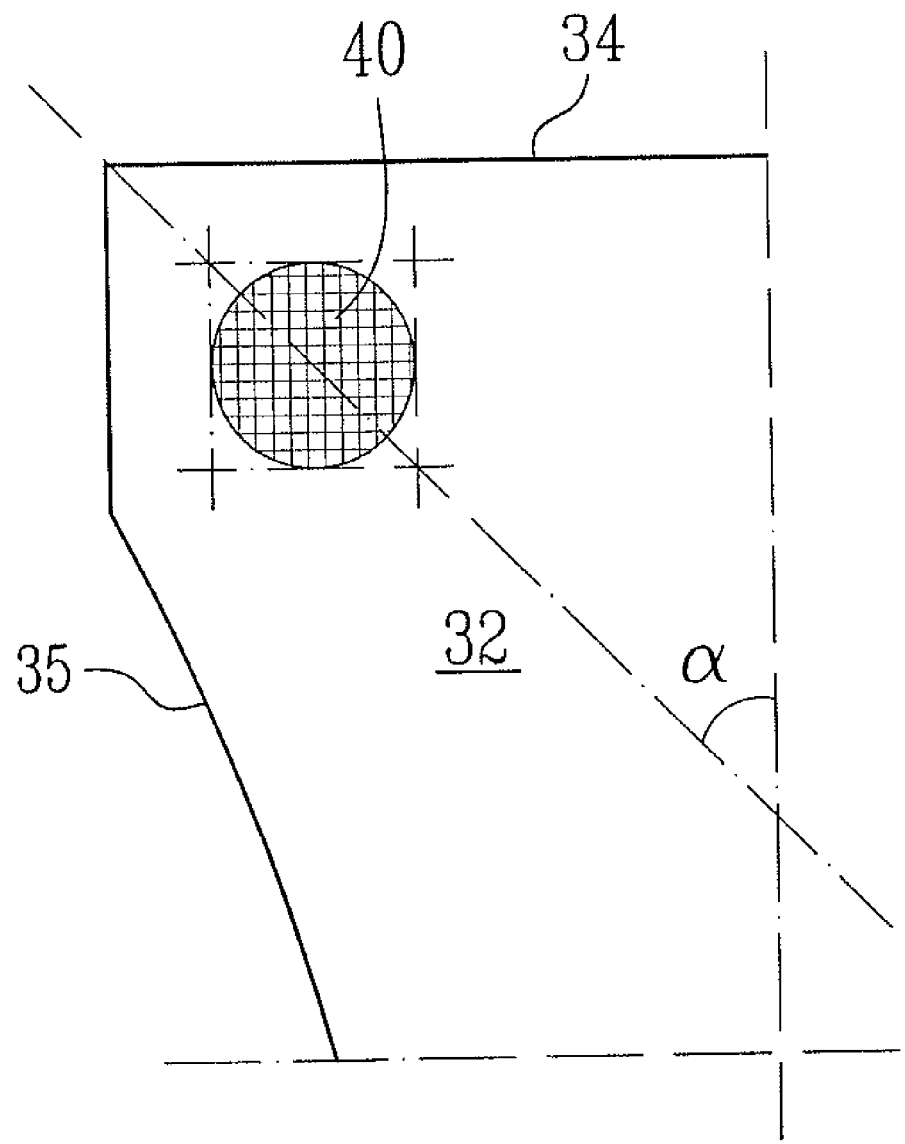
FIG. 3 shows a close-up of the second longitudinal end region of the article.

The article fastening means 40 of the invention has a substantially circular shape in the L-T plane, as shown in FIGS. 1-3. By "substantially circular" is meant that it may be oval, elliptical, egg-shaped, or a flattened circle. Preferably, though, the article fastening means 40 has a circular shape.

The article fastening means 40 of the invention avoids the presence of sharp (acute) angles in the region outside the force line (X). This reduces the tendency for the article fastening means 40 to turn up or become uncovered in use. The article fastening means 40 of the invention also reduces the extension of the article fastening means 40 in the region outside the force line (X) as compared to article fastening means 40 of the prior art.

The maximum extension of the article fastening means 40 in a direction perpendicular to a force line (X) which passes through the centre of the circular article fastening means 40 and which makes an angle with the longitudinal centre line (L1) of the absorbent structure 30 of between 5° and 85°, preferably between 10° and 80°, more preferably between 15° and 45° is suitably less than 3 cm, preferably less than 2 cm, more preferably less than 1 cm.

The invention has been described with reference to a number of embodiments and accompanying Figures. However, the full scope of the invention is determined by the appended claims.

The invention claimed is:

1. An absorbent article, said article comprising a belt and an absorbent structure;
    said belt comprising an article reception surface, said article reception surface being located on the outside (garment-facing) surface of the belt when the article is worn;
    said absorbent structure extending in longitudinal and transverse directions and having a longitudinal centre line and opposing first and second longitudinal end regions;
    each of said longitudinal end regions having a perimeter constituted by a transversely extending end edge and a pair of opposed longitudinal edges,
    said first longitudinal end region of said absorbent structure being attached to the belt;
    said absorbent structure comprising two article fastening elements at the second longitudinal end region thereof, said article fastening elements adapted to fasten to the article reception surface on the belt such that the absorbent article adopts a pant shape in use;
    wherein
    said article fastening elements have a circular shape in the longitudinal-transverse plane, and
    wherein the maximum extension of the article fastening elements in a direction perpendicular to a force line which passes through a centre of the circular article fastening elements and which makes an angle with the longitudinal centre line of the absorbent structure of between 5° and 85° is less than 3 cm.

2. The absorbent article according to claim 1, wherein the first longitudinal end of said absorbent structure is attached to the belt via at least one article fastening element located at the first longitudinal end of the absorbent structure, said article fastening element having a circular shape.

3. The absorbent article according to claim 2, wherein the first longitudinal end of said absorbent structure is permanently attached to the belt.

4. The absorbent article according to claim 2, wherein the belt consists of the article reception surface on the garment-facing side thereof.

5. The absorbent article according to claim 1, wherein the first longitudinal end of said absorbent structure is permanently attached to the belt.

6. The absorbent article according to claim 5, wherein the belt consists of the article reception surface on the garment-facing side thereof.

7. The absorbent article according to claim 1, wherein the belt consists of the article reception surface on the garment-facing side thereof.

8. The absorbent article according to claim 1, the absorbent article being a diaper or an incontinence guard.

9. The absorbent article according to claim 1, wherein the force line makes an angle with the longitudinal centre line of the absorbent structure of between 15° and 45°.

10. The absorbent article according to claim 1, wherein the maximum extension is less than 2 cm.

11. The absorbent article according to claim 1, wherein the maximum extension is less than 1 cm.

12. The absorbent article according to claim 1, wherein the belt includes a transversely extending edge, and the transversely extending edge of the belt and the transversely extending end edges of the absorbent structure are arranged to be substantially parallel.

* * * * *